United States Patent
Tonn et al.

(10) Patent No.: US 11,534,226 B2
(45) Date of Patent: Dec. 27, 2022

(54) SYSTEMS AND METHODS FOR MINIMIZING ARCING OF BIPOLAR FORCEPS

(71) Applicant: COVIDIEN LP, Mansfield, MA (US)

(72) Inventors: Donald L. Tonn, Superior, CO (US); James E. Dunning, Lafayette, CO (US); William D. Faulkner, Boulder, CO (US); Jennifer R. McHenry, Denver, CO (US); Devon E. Scott-Drechsel, Superior, CO (US); Eric M. Westra, Loveland, CO (US)

(73) Assignee: Covidien LP, Mansfield, MA (US)

( * ) Notice: Subject to any disclaimer, the term of this patent is extended or adjusted under 35 U.S.C. 154(b) by 650 days.

(21) Appl. No.: 16/122,846

(22) Filed: Sep. 5, 2018

(65) Prior Publication Data
US 2019/0090931 A1    Mar. 28, 2019

Related U.S. Application Data

(60) Provisional application No. 62/562,012, filed on Sep. 22, 2017, provisional application No. 62/562,078, (Continued)

(51) Int. Cl.
*A61B 18/12*    (2006.01)
*A61B 18/14*    (2006.01)
(Continued)

(52) U.S. Cl.
CPC .......... *A61B 18/1206* (2013.01); *A61B 18/14* (2013.01); *A61B 2018/0063* (2013.01); (Continued)

(58) Field of Classification Search
CPC .......... A61B 2018/00642; A61B 2018/00666; A61B 2018/00672; A61B 2018/00678; (Continued)

(56) References Cited

U.S. PATENT DOCUMENTS 4,727,874 A * 3/1988 Bowers .............. A61B 18/1206
                                                     330/251
5,472,443 A    12/1995 Cordis et al.
(Continued)

FOREIGN PATENT DOCUMENTS

CN    102156760 A  *  8/2011
DE    179607 C        3/1905
(Continued)

OTHER PUBLICATIONS

CN 102156760 A (Univ Beihang). Translated by IP.com. retrieved on Jul. 23, 2021 (Year: 2010).*

(Continued)

*Primary Examiner* — Michael F Peffley
*Assistant Examiner* — Nicholas S Borsch
(74) *Attorney, Agent, or Firm* — Carter, DeLuca & Farrell LLP

(57) ABSTRACT

An electrosurgical generator includes a processor and a memory storing instructions executable by the processor. The instructions when executed, cause the generator to provide an indicated treatment energy to the instrument, where the indicated treatment energy is set by a user and having a corresponding current limit, receive signals from the instrument over time relating to a load impedance between the active electrode and the return electrode of the instrument, determine based on the signals that the active electrode and the return electrode are currently shorted together, and prior to the short, the instrument was grasping tissue between the active electrode and the return electrode, and based on the determination, reduce a current limit of treatment energy being provided to the instrument to below the corresponding current limit.

16 Claims, 4 Drawing Sheets

Related U.S. Application Data filed on Sep. 22, 2017, provisional application No. 62/562,110, filed on Sep. 22, 2017.

(51) Int. Cl.
*A61B 18/00* (2006.01)
*A61B 90/00* (2016.01)

(52) U.S. Cl.
CPC ............... *A61B 2018/0072* (2013.01); *A61B 2018/00589* (2013.01); *A61B 2018/00601* (2013.01); *A61B 2018/00642* (2013.01); *A61B 2018/00648* (2013.01); *A61B 2018/00666* (2013.01); *A61B 2018/00678* (2013.01); *A61B 2018/00702* (2013.01); *A61B 2018/00767* (2013.01); *A61B 2018/00827* (2013.01); *A61B 2018/00875* (2013.01); *A61B 2018/00892* (2013.01); *A61B 2018/00898* (2013.01); *A61B 2018/126* (2013.01); *A61B 2018/1213* (2013.01); *A61B 2018/1462* (2013.01); *A61B 2090/065* (2016.02)

(58) Field of Classification Search
CPC .. A61B 2018/00702; A61B 2018/0072; A61B 2018/00755; A61B 2018/00767; A61B 2018/00875; A61B 2018/00988; A61B 18/1442; A61B 18/1445; A61B 2018/1462; A61B 2018/1475; A61B 2018/1467; A61B 2018/00648; A61B 18/1233; A61B 18/1206; A61B 18/14; A61B 2018/1213

See application file for complete search history.

(56) References Cited

U.S. PATENT DOCUMENTS

| | | | |
|---|---|---|---|
| 6,080,149 A | 6/2000 | Huang et al. | |
| 6,468,270 B1 | 10/2002 | Hovda et al. | |
| 6,837,888 B2 | 1/2005 | Ciarrocca et al. | |
| 6,942,660 B2 | 9/2005 | Pantera et al. | |
| 6,974,453 B2 | 12/2005 | Woloszko et al. | |
| D574,323 S | 8/2008 | Waaler | |
| 7,651,492 B2 | 1/2010 | Wham | |
| 9,270,202 B2 | 2/2016 | Johnson et al. | |
| 9,283,028 B2 | 3/2016 | Johnson | |
| 10,702,337 B2* | 7/2020 | Waldstreicher | A61N 1/06 |
| 2002/0029036 A1 | 3/2002 | Goble et al. | |
| 2002/0032439 A1 | 3/2002 | Hareyama | |
| 2002/0165531 A1 | 11/2002 | Goble | |
| 2004/0167508 A1 | 8/2004 | Wham et al. | |
| 2005/0203504 A1 | 9/2005 | Wham et al. | |
| 2006/0217707 A1 | 9/2006 | Daniel et al. | |
| 2007/0173811 A1 | 7/2007 | Couture et al. | |
| 2007/0265616 A1 | 11/2007 | Couture et al. | |
| 2008/0221565 A1 | 9/2008 | Eder et al. | |
| 2008/0287944 A1 | 11/2008 | Pearson et al. | |
| 2009/0240244 A1 | 9/2009 | Malis et al. | |
| 2009/0248007 A1 | 10/2009 | Falkenstein et al. | |
| 2011/0028963 A1 | 2/2011 | Gilbert | |
| 2011/0037484 A1 | 2/2011 | Gilbert | |
| 2011/0038056 A1 | 2/2011 | Nakamura | |
| 2011/0208183 A1 | 8/2011 | Stockert | |
| 2012/0078139 A1 | 3/2012 | Aldridge et al. | |
| 2012/0116391 A1* | 5/2012 | Houser | A61B 18/1442 606/41 |
| 2012/0179154 A1 | 7/2012 | Goldberg et al. | |
| 2014/0100559 A1 | 4/2014 | Wham et al. | |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0257270 A1 | 9/2014 | Behnke | |
| 2014/0258800 A1 | 9/2014 | Gilbert | |
| 2014/0276659 A1 | 9/2014 | Juergens et al. | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088117 A1 | 3/2015 | Gilbert et al. | |
| 2015/0088118 A1 | 3/2015 | Gilbert et al. | |
| 2015/0088122 A1* | 3/2015 | Jensen | A61B 18/1445 606/37 |
| 2015/0088124 A1 | 3/2015 | Wham | |
| 2015/0088125 A1 | 3/2015 | Wham | |
| 2015/0119871 A1 | 4/2015 | Johnson et al. | |
| 2015/0289925 A1* | 10/2015 | Voegele | A61B 18/1233 606/51 |
| 2017/0105791 A1* | 4/2017 | Yates | A61B 18/18 |
| 2018/0333182 A1* | 11/2018 | Clauda | A61B 18/00 |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 2111812 A2 | 10/2009 |
| EP | 2649956 A1 | 10/2013 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |

(56) References Cited

FOREIGN PATENT DOCUMENTS

| JP | 2002065690 A | 3/2002 |
|---|---|---|
| JP | 2005185657 A | 7/2005 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006/050888 A1 | 5/2006 |
| WO | 2008053532 A1 | 5/2008 |
| WO | 2008071914 A2 | 6/2008 |

OTHER PUBLICATIONS

European Office Action dated Dec. 12, 2020 corresponding to counterpart Patent Application EP 18195884.4.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence" Am. J. Ml, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
Chinese First Office Action dated Nov. 4, 2020 corresponding to counterpart Patent Application CN 201811104579.0.
Extended European Search Report issued in corresponding EP Application No. 18195884.4 dated Dec. 10, 2018, 9 pages.
Japanese Office Action dated Jul. 18, 2019 corresponding to counterpart Patent Application JP 2018-177155.

\* cited by examiner

SYSTEMS AND METHODS FOR MINIMIZING ARCING OF BIPOLAR FORCEPS

CROSS-REFERENCE TO RELATED APPLICATIONS

The present application claims priority to U.S. Provisional Application No. 62/562,012, filed on Sep. 22, 2017, U.S. Provisional Application No. 62/562,078, filed on Sep. 22, 2017, and U.S. Provisional Application No. 62/562,110, filed on Sep. 22, 2017. The entire contents of each of the foregoing applications are hereby incorporated by reference.

BACKGROUND

1. Technical Field

The present disclosure generally relates to electrosurgical generators. More particularly, the present disclosure relates to electrosurgical systems and methods for providing, controlling, and applying electrosurgical energy for dissection of tissue.

2. Background of Related Art

An electrosurgical generator is used in surgical procedures to provide electrical energy for treating the tissue of a patient. When bipolar forceps or another electrosurgical instrument is connected to the generator, the instrument can be used for cutting, coagulation, or sealing the tissue of a patient with high frequency electrical energy. During operation, electrical current from the generator flows between an active electrode and a return electrode of the instrument by passing through tissue and bodily fluids of a patient.

The electrical energy provided by the electrosurgical generator has different waveforms shaped to enhance its ability to cut, coagulate, or seal tissue. Different waveforms correspond to different modes of operating the generator, and each mode provides the surgeon various operating advantages. A surgeon can select and change various modes of operation as the surgical procedure progresses.

In the various modes, it is important to apply the appropriate amount of energy for the electrosurgical procedure. For example, applying too much energy may result in dissection or destruction of tissue. Applying too little energy may result in inhibiting the surgical procedure. Therefore, it is desirable to control the amount of energy provided by the electrosurgical generator for the surgical procedure being performed and for the operating conditions that are encountered. Accordingly, there is continued interest in developing and improving the control of electrical energy provided by an electrosurgical generator.

SUMMARY

The electrosurgical systems and methods of the present disclosure relate to systems and methods for providing, controlling, and applying electrosurgical energy for dissection of tissue. As will be described herein in more detail, when tissue is grasped between the active and return electrodes of an electrosurgical instrument for dissection, and then the active and return electrodes become shorted together, electrosurgical energy provided to the instrument can be controlled by reducing a current limit of the electrosurgical energy to prevent unwanted arcing between the active and return electrodes.

In accordance with aspects of the present disclosure, the present disclosure includes an electrosurgical generator for providing electrical treatment energy to an instrument. The generator includes a processor and a memory storing instructions which are executable by the processor. When the instructions are executed, they cause the generator to provide an indicated treatment energy to the instrument where the indicated treatment energy is set by a user and has a corresponding current limit, receive signals from the instrument over time relating to a load impedance between the active electrode and the return electrode of the instrument, determine that the active electrode and the return electrode are currently shorted together and that, prior to the short, the instrument was grasping tissue between the active electrode and the return electrode, and based on that determination, reduce a current limit of treatment energy being provided to the instrument to below the corresponding current limit.

In various embodiments, the current limit is less than a maximum current that is capable of being provided to the instrument.

In various embodiments, the memory stores further instructions which, when executed by the processor, causes the generator to determine that the instrument was grasping tissue and that the active electrode and the return electrode are currently shorted together based on the load impedance decreasing from above a threshold to below the threshold. In various embodiments, the load impedance threshold is approximately four ohms.

In various embodiments, the indicated treatment energy has a corresponding voltage limit. In various embodiments, the memory stores further instructions which, when executed by the processor, further cause the generator to receive further signals from the instrument relating to the load impedance between the active electrode and the return electrode, determine based on the further signals that the load impedance is above a threshold, and based on the determination that the load impedance is above the threshold, reducing a voltage limit of treatment energy being provided to the instrument to below the corresponding voltage limit. In various embodiments, the corresponding voltage limit is less than a maximum voltage that is capable of being provided to the instrument.

In accordance with aspects of the present disclosure, the present disclosure includes a method in for providing electrical treatment energy to an instrument having an active electrode and a return electrode. The method includes providing an indicated treatment energy to the instrument, where the indicated treatment energy is set by a user and has a corresponding current limit, receiving signals from the instrument over time relating to a load impedance between the active electrode and the return electrode of the instrument, determining based on the signals that the active electrode and the return electrode are currently shorted together and that, prior to the short, the instrument was grasping tissue between the active electrode and the return electrode, and reducing, based on the determination, a current limit of treatment energy being provided to the instrument to below the corresponding current limit. In various embodiments, the electrosurgical generator includes an indicator that is configured to indicate that the active and return electrodes are shorted. In various embodiments, the indicator can be, for example, a graphical user interface, an alert sound, a light, or another type of indicator.

In various embodiments, the corresponding current limit is less than a maximum current that is capable of being provided to the instrument. In various embodiments, the disclosed method includes determining that the instrument was grasping tissue and that the active electrode and the return electrode are shorted together based on the load impedance decreasing from above a threshold to below the threshold. In various embodiments, the load impedance threshold is approximately four ohms.

In various embodiments, the indicated treatment energy has a corresponding voltage limit, and the disclosed method includes receiving further signals from the instrument relating to the load impedance between the active electrode and the return electrode, determining based on the further signals that the load impedance is above a threshold, and based on the determination that the load impedance is above the threshold, reducing a voltage limit of treatment energy being provided to the instrument to below the corresponding voltage limit. In various embodiments, the corresponding voltage limit is less than a maximum voltage that is capable of being provided to the instrument.

In accordance with aspects of the present disclosure, the present disclosure includes a system for treating tissue. The system includes an electrosurgical generator and an electrosurgical instrument configured to receive electrical treatment energy and to treat tissue. The electrosurgical generator includes a processor and a memory storing instructions executable by the processor. When the instructions are executed, they cause the generator to provide an indicated treatment energy to the instrument where the indicated treatment energy is set by a user and has a corresponding current limit, receive signals from the instrument over time relating to a load impedance between the active electrode and the return electrode of the instrument, determine based on the signals that the active electrode and the return electrode are shorted together and that, prior to the short, the instrument was grasping tissue between the active electrode and the return electrode, and based on the determination, reduce a current limit of treatment energy being provided to the instrument to below the corresponding current limit.

BRIEF DESCRIPTION OF THE DRAWINGS

Various embodiments of the present disclosure are described with reference to the accompanying drawings wherein.

DETAILED DESCRIPTION

The present disclosure relates to systems and methods for providing, controlling, and applying electrosurgical energy for dissection of tissue. As will be described herein in more detail, in one aspect of the present disclosure, when tissue is grasped between the active and return electrodes of an electrosurgical instrument for dissection, and then the active and return electrodes become shorted together, electrosurgical energy provided to the instrument can be controlled by reducing a current limit of the electrosurgical energy to prevent unwanted arcing between the active and return electrodes.

Where the term "approximately" is used herein in connection with a parameter having approximately a value, it is intended that the parameter can have exactly the value or can have another value which differs from the value due to environmental factors such as noise or due to hardware or software limitations such as, for example, number of bits, processor speed, or interrupt priority.

Figure 1:
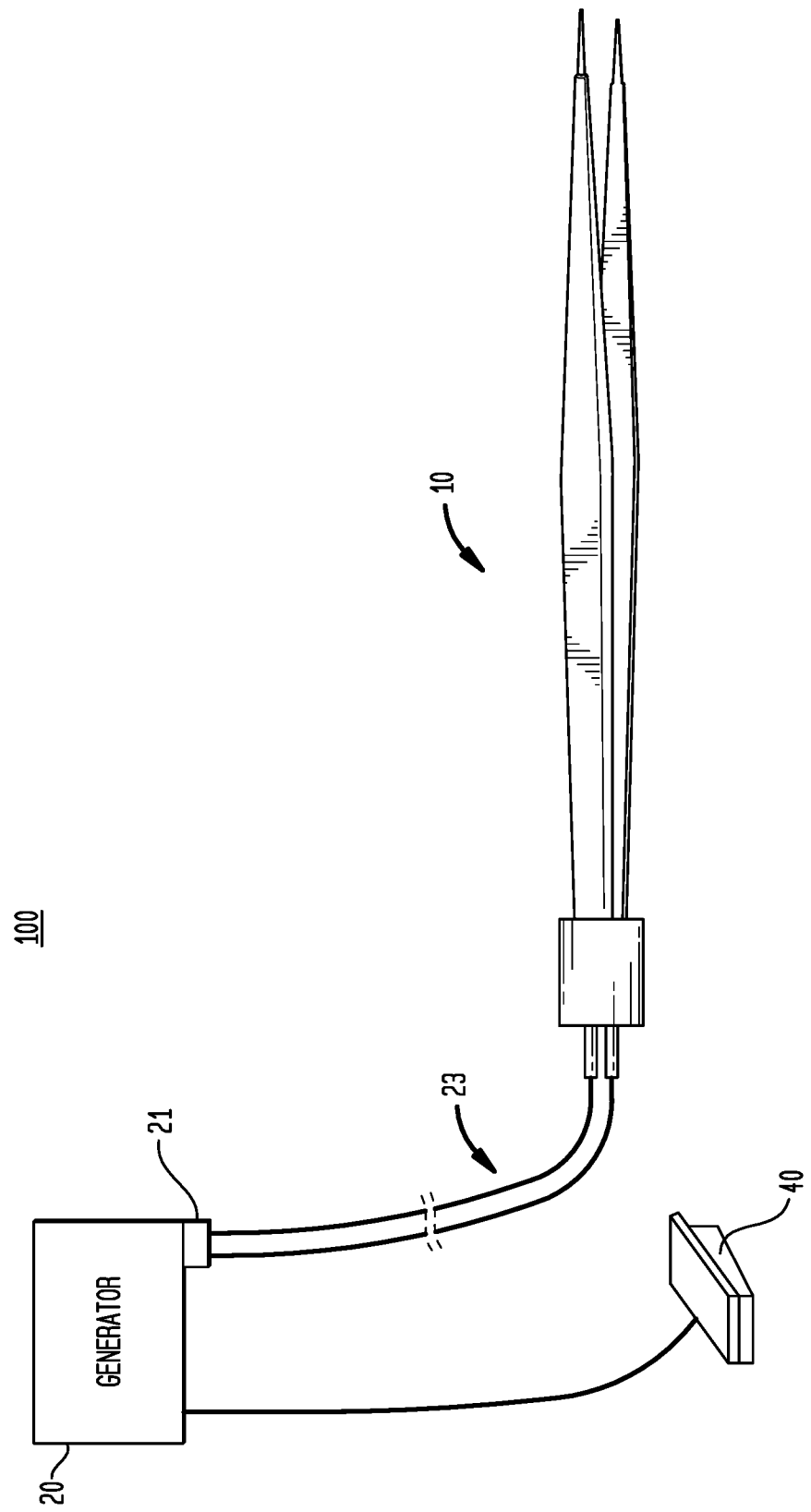
FIG. 1 is a schematic illustration, which shows an exemplary electrosurgical system including an electrosurgical generator in accordance with aspects of the present disclosure.

Referring now to FIG. 1, there is shown an illustration of an exemplary electrosurgical system 100 in accordance with aspects of the present disclosure. The system 100 includes an electrosurgical generator 20, an electrosurgical instrument 10, a cable 23 connecting the generator 20 and the instrument 10, and a foot switch 40. In various embodiments, the cable 23 and the instrument 10 may be separable. In various embodiments, the cable 23 may be attached to the instrument 10 and may be inseparable from the instrument 10. The generator 20 includes a port 21 that receives the cable 23. In various embodiments, the instrument 10 is a bipolar instrument and the port 21 of the generator 20 is a bipolar instrument port. As persons skilled in the art will recognize, a bipolar instrument receives electrical energy from a generator, applies a portion thereof to treat tissue through an active electrode, and returns a portion of the energy back to the generator through a return electrode. The instrument 10 illustrated in FIG. 1 is an exemplary bipolar forceps, which will be described in more detail in connection with FIG. 3. In various embodiments, the instrument 10 can be another type of bipolar electrosurgical instrument.

With continuing reference to FIG. 1, the generator 20 includes a user interface (not shown) that enables a user to set the generator 20 to provide electrical energy for different types of procedures. In various embodiments, the generator 20 can provide electrical energy for vessel coagulation, tissue dissection, or other types of electrosurgical procedures. Persons skilled in the art will understand the electrosurgical parameters generally suitable for such procedures. In various embodiments, the user interface (not shown) can include an energy setting that permits a user to specify an electrical energy for the generator 20 to provide to the instrument 10.

In FIG. 1, the system 100 also includes a foot switch 40 that is in communication with the generator 20. The foot switch 40 can be depressed to indicate to the generator 20 that electrical energy should be activated and provided to the instrument 10, and release of the foot switch 40 can indicate to the generator 20 that electrical energy should be deactivated. The illustrated embodiment of FIG. 1 is exemplary, and configurations, components, and devices other than those illustrated are contemplated to be within the scope of the present disclosure.

Figure 2:
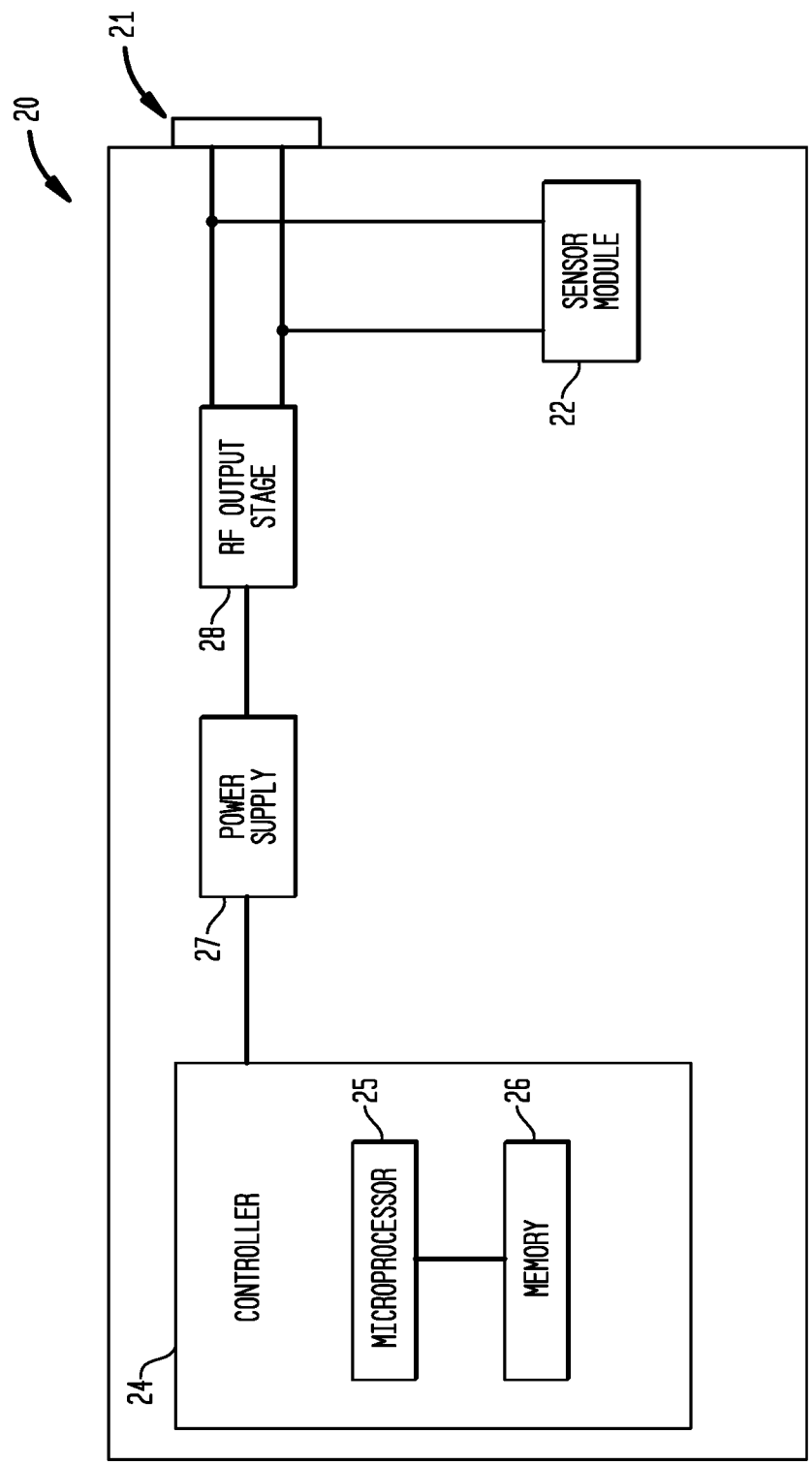
FIG. 2 shows a block diagram of exemplary components of the electrosurgical generator of FIG. 1 in accordance with aspects of the present disclosure.

Referring now to FIG. 2, there is shown a block diagram of exemplary components of an electrosurgical generator 20 in accordance with aspects of the present disclosure. In the illustrated embodiment, the generator 20 includes a controller 24, a power supply 27, a radio-frequency (RF) energy output stage 28, a sensor module 22, and one or more connector ports 21 that accommodate various types of electrosurgical instruments. The generator 20 can include a user interface (not shown), which permits a user to select various parameters for the generator 20, such as mode of operation and power setting. The mode of operation can include, for example, coagulation mode and tissue dissection mode. In various embodiments, the power setting can be specified by a user to be between zero and a power limit, such as, for example, five watts, thirty watts, seventy watts, or ninety-five watts.

In the illustrated embodiment, the controller 24 includes a microprocessor 25 and a memory 26. In various embodiments, the controller 24 or the microprocessor 25 may be another type of processor such as, without limitation, a digital signal processor, field-programmable gate array (FPGA), or a central processing unit (CPU). In various embodiments, the memory 26 can be random access memory, read only memory, magnetic disk memory, solid state memory, optical disc memory, and/or another type of memory. In various embodiments, the memory 26 can be separate from the controller 24 and can communicate with the microprocessor 25 through communication buses of a circuit board and/or through communication cables such as serial ATA cables or other types of cables. The memory 26 includes machine instructions that are executable by the microprocessor 25 to operate the generator 20. Various operations of the generator 20 are described below. Such operations can be controlled by the machine instructions executed by the microprocessor 25.

With continuing reference to FIG. 2, in various embodiments, the power supply 27 can be a converter that receives AC energy, such as AC energy from a wall outlet, and converts the AC energy to DC energy. The power supply 27 can provide power to the controller 24 and can also be controllable by the controller 24. For example, the controller 24 can control the power supply 27 based on a user-specified power setting. The DC energy produced by the power supply 27 is conveyed to the RF energy output stage 28. In various embodiments, the RF output stage 28 converts the DC energy into an AC electrical waveform and conveys the waveform to an electrosurgical instrument through the connector port 21. In various embodiments, the RF output stage 28 can include an H-bridge that drives a resonant tank. Persons skilled in the art will understand the various implementations of the power supply 27 and the RF output stage 28, and will understand the AC electrical waveforms suitable for coagulation, tissue dissection, and other operations.

With continuing reference to FIG. 2, the sensor module 22 can include a voltage sensor and a current sensor, among other types of sensors. In various embodiments, the sensor module 22 and the controller 24 can cooperate to determine or estimate a load impedance of a load of the instrument. For example, the controller 24 can direct the RF output stage 28 to generate a non-therapeutic electrical waveform that can be used to determine or estimate a load impedance of a load of the instrument. The non-therapeutic electrical waveform corresponds to a voltage and current provided from the generator 20 to the instrument through the connector port 21 and corresponds to a return current that returns from the instrument to the generator 20 through the connector port 21. The return current can be sensed by the sensor module 22, which can communicate the return current measurements to the controller 24. The controller 24 can use the return current measurements to determine or estimate the load impedance of a load of the instrument. For example, the load impedance can be determined or estimated as the voltage provided by the RF output stage 28 divided by the sensed return current. In various embodiments, the voltage sensor of the sensor module 22 can sense the voltage provided to the connector port 21, and the sensed voltage can be used with the sensed return current to determine or estimate the load impedance of a load of the instrument. For example, the load impedance can be determined or estimated as the sensed voltage divided by the sensed return current.

As will be described in more detail in connection with FIG. 4, if the load impedance is greater than a predetermined threshold, such as approximately eight-thousand (8000) ohms, the controller 24 can determine that the instrument is not grasping tissue. On the other hand, if the load impedance is less than a predetermined threshold, such as approximately four ohms, the controller 24 can determine that the active and return electrodes of the instrument are shorted together. Otherwise, the controller 24 can determine that the instrument is grasping tissue.

In various embodiments, the controller 24 and the sensor module 22 can determine whether the instrument is grasping tissue in other ways. As mentioned above, a user can set an energy setting at the generator 20, and the generator 20 can control the voltage and/or current provided by the power supply 27 and RF output stage 28 to provide the indicated energy. When the instrument is not grasping tissue, no meaningful current is drawn by the instrument. Thus, no treatment energy is actually provided by the generator 20 to the instrument, and the voltage at the output of the RF output stage 28 stays essentially the same. When the instrument grasps tissue, a current is then drawn by the instrument, which causes the generator 20 to vary the voltage to provide the indicated treatment energy setting. The variations in voltage can be characterized using a parameter known as crest factor, which persons skilled in the art will understand as a ratio of peak voltage to root-mean-squared (RMS) voltage. In various embodiments, the sensor module 22 can include one or more voltage sensors that measure voltages and can communicate the measurements to the controller 24 for the purpose of determining crest factor. In various embodiments, if the crest factor is greater than a predetermined threshold, the controller can determine that the instrument has grasped tissue. The illustrated embodiment of FIG. 2 is exemplary, and configurations, components, and devices other than those illustrated are contemplated to be within the scope of the present disclosure.

Figure 3:
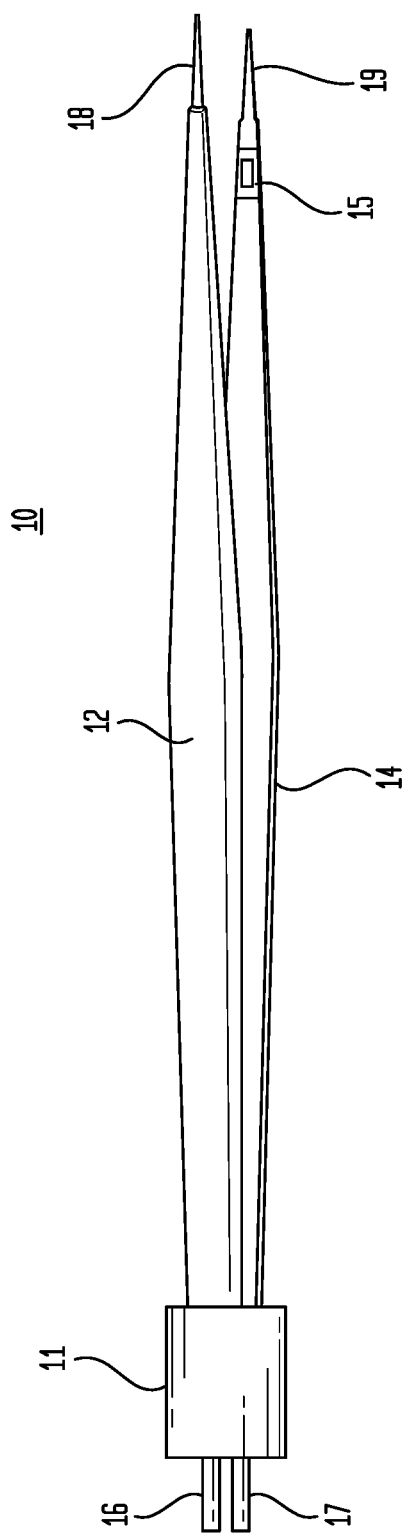
FIG. 3 shows a diagram of the electrosurgical instrument of FIG. 1.

FIG. 3 is an illustration of an exemplary instrument in accordance with aspects of the present disclosure. The instrument illustrated in FIG. 3 is a bipolar forceps 10, which may be used for various procedures such as vessel coagulation and tissue dissection. The bipolar forceps 10 includes an electrical connector 11 with two terminals 16, 17 configured to connect to an electrosurgical generator through a cable. One terminal 16 conveys current from the generator to the instrument 10, and the other terminal 17 returns current from the instrument 10 back to the generator.

The electrical connector 11 is attached to two arms 12, 14 that extend from the electrical connector 11. The two arms 12, 14 terminate in electrodes 18, 19 at the end opposite the electrical connector 11. One electrode 18 is referred to herein as an active electrode, and the other electrode 19 is referred to as a return electrode. The active electrode 18 conveys current received from the generator, and the return electrode 19 returns current back to the generator. The two arms 12, 14 include conductors (not shown) that connect the terminals 16, 17 of the electrical connector 11 with the electrodes 18, 19. Additionally, the two arms 12, 14 are mechanically biased away from each other so that the arms 12, 14 are apart in their resting state. A surgeon using the bipolar forceps 10 can squeeze the arms 12, 14 with varying amounts of force to press the arms 12, 14 and the electrodes 18, 19 closer together and to grasp tissue between the electrodes 18, 19.

When using the bipolar forceps 10 to dissect tissue, it is possible for the electrodes 18, 19 to become shorted together. For example, when a surgeon squeezes the arms 12, 14 to grasp tissue, the electrodes 18, 19 are pressed closer together. As long as tissue is still grasped and the dissection procedure is in progress, the electrodes 18, 19 will not be shorted. However, once the tissue is dissected, continued squeezing of the arms 12, 14 at that point can cause the electrodes 18, 19 to become shorted together and overheat and an arc may form. Thus, it is beneficial to determine whether the instrument is grasping or still grasping tissue.

In accordance with one aspect of the present disclosure, the instrument 10 can include one or more sensors 15 for determining whether the instrument 10 is grasping tissue. In connection with FIG. 3, the sensor 15 can be located on one or both of the arms 12, 14. In various embodiments, the sensor 15 can be a pressure sensor that indicates whether tissue is in contact with the pressure sensor. In various embodiments, the sensor 15 can be a light sensor that indicates whether tissue is occluding light from reaching the light sensor. The pressure sensor and/or the light sensor can be located in proximity to the active and return electrodes 18, 19, such that the sensor signals are indicative or whether the active and return electrodes 18, 19 are grasping tissue. In various embodiments, the sensor 15 can be arranged at another location of the instrument 10 as long as the sensor signals would be indicative of whether the active and return electrodes 18, 19 are grasping tissue. In various embodiments, the instrument 10 can include a manual switch (not shown) which a user can toggle to manually indicate whether tissue is grasped by the instrument 10. The signals from the pressure sensor, the light sensor, or the manual switch can be communicated from the instrument 10 to the generator. In various embodiments, the signals can be communicated using the terminals 16, 17 of the electrical connector 11. In various embodiments, the signals can be communicated using another conductor in the cable (FIG. 1, 23) connecting the instrument 10 and the generator, and the electrical connector 11 can include a third terminal (not shown) for this communication.

The illustrated embodiment of FIG. 3 is exemplary, and other instruments are contemplated to be within the scope of the present disclosure. In various embodiments, the instrument 10 can be another electrosurgical instrument that permits a surgeon to exert varying degrees of pressure on tissue by applying varying degrees of force to the instrument, such as Kleppinger forceps.

What have been described above are systems, methods, and devices for producing, controlling, and applying electrosurgical energy. The following will describe methods for controlling electrosurgical energy during a tissue dissection procedure.

As described above, when using bipolar forceps for electrosurgical procedures such as dissection, there may be occasions where the electrodes of the forceps will become shorted together. This short can result in a large amount of current provided by the generator being delivered through the forceps, resulting in a great deal of heating of and wear on the forceps electrodes. The heating and wear may cause the forceps electrodes to stick together as a result, requiring the surgeon to forcibly separate the electrodes. Then, when the surgeon opens the electrodes after they were just shorted to each other, the sudden opening stops current flow between the electrodes and causes the generator to react by quickly increasing voltage, which can cause arcing between the electrodes. Such arcing may cause pitting and electrode destruction, which would cause the return and active electrodes to be more sticky to tissue.

In accordance with an aspect of the present disclosure, when it is determined that an electrosurgical instrument's electrodes are shorted together, the heating of the instrument's electrodes can be mitigated by reducing a current limit of treatment energy provided by the generator to the instrument, and notifying the surgeon of the short condition. Then, when it is determined that the instrument's electrodes are separated, arcing between the electrodes can be mitigated by reducing a voltage limit of treatment energy provided by the generator to the instrument. In this case, rather than simply reducing the voltage provided by the generator to the instrument, the present disclosure reduces the voltage limit instead.

With reference to FIG. 2, the current limit and the voltage limit can be parameters stored in the memory 26, and they can be adjustable. The current limit parameter is not the maximum current that the generator 20 could provide to the instrument. Rather, the current limit parameter specifies a current that the generator 20 will not exceed in providing electrical energy to the instrument. In various embodiments, if the current exceeds the current limit, the generator 20 can reduce the current to the current limit or below the current limit. Similarly, the voltage limit parameter is not the maximum voltage that the generator 20 could provide to the instrument. Rather, the voltage limit parameter specifies a voltage that the generator 20 will not exceed in providing electrical energy to the instrument. In various embodiments, if the voltage exceeds the voltage limit, the generator 20 can reduce the voltage to the voltage limit or below the voltage limit. In enforcing the voltage limit and the current limit, the sensor module 22 can sense the voltage and current values provided to the instrument and can communicate these sensed values to the controller 24. The controller 24 can use the sensed current and voltage values to enforce the current and voltage limits.

Figure 4:
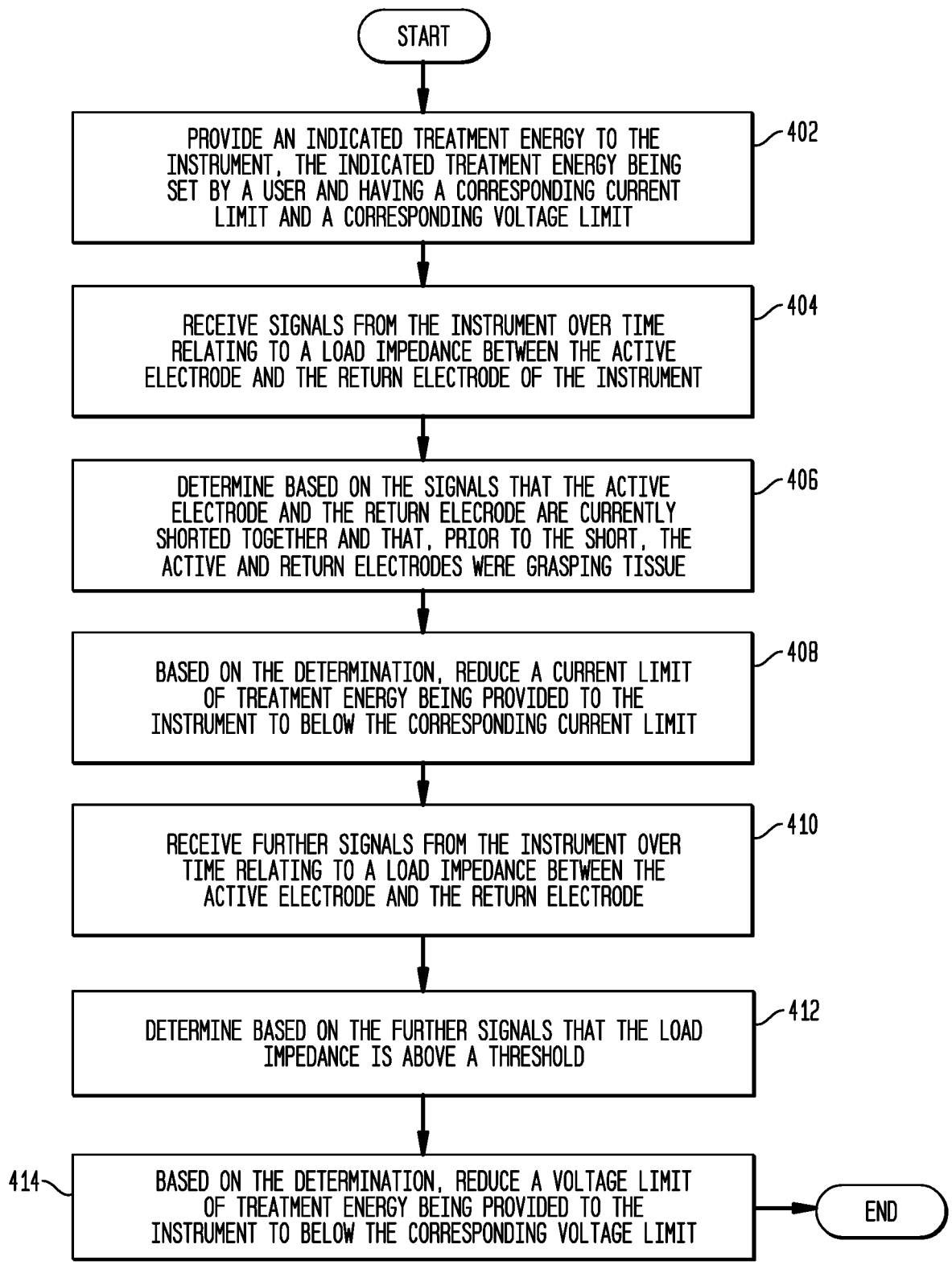
FIG. 4 shows a flow chart of an exemplary operation of an electrosurgical system in accordance with aspects of the present disclosure.

FIG. 4 shows a flow diagram of a method for a generator to reduce a current limit of treatment energy being provided to the instrument in accordance with aspects of the present disclosure. The disclosed method can be implemented in whole or in part by machine instructions stored in memory and executed on a processor. In various embodiments, the disclosed method can be implemented by a field-programmable gate array.

With reference also to FIG. 1, at step 402, the generator 20 can provide an indicated treatment energy to the instrument 10. As described above herein, the treatment energy can be set by a user using a user interface of the generator 20. In various embodiments, the indicated treatment energy can be, for example, a power between approximately one and ninety-five watts. In accordance with an aspect of the present disclosure, the treatment energy has a corresponding current limit such that, in providing the treatment energy, the generator provides current only up to the current limit or reduces current down to the current limit. In various embodiments, each treatment energy setting has a corresponding current limit, and higher energy settings can have higher current limits. In various embodiments, the current limit can be approximately two amperes.

With reference also to FIG. 3, at step 404, the generator 20 can receive signals from the instrument 10 over time relating to a load impedance between the active electrode 18 and the return electrode 19 of the instrument 10. As discussed in connection with FIG. 2, the signals can be return current returned from the instrument 10 to the generator 20 based on a non-therapeutic electrical waveform.

At step 406, the signals received by the generator 20 can be used by the generator 20 to determine that the active electrode 18 and the return electrode 19 are currently shorted together and that, prior to the short, the active electrode 18 and the return electrode 19 were grasping tissue. As described in connection with FIG. 2, load impedance can be used to determine whether or not the instrument 10 is grasping tissue. If the load impedance is less than a predetermined threshold, such as approximately four ohms, the controller 24 can determine that the active and return electrodes of the instrument are shorted together. If the load impedance is greater than the predetermined threshold and is lower than another predetermined threshold, such as approximately eight-thousand (8000) ohms, the controller 24 can determine that the instrument is grasping tissue. Thus, the load impedance determined by the controller 24 over time can indicate that the active electrode 18 and the return electrode 19 are currently shorted together because the load impedance is currently lower than approximately four ohms. Prior to the short, the load impedance determined by the controller 24 can indicate that the active electrode 18 and the return electrode 19 are grasping tissue because the load impedance is greater than approximately four ohms but lower than approximately eight-thousand (8000) ohms.

At step 408, when the controller (FIG. 2, 24) determines that the active and return electrodes of the instrument 10 are shorted together, the generator 20 reduces the current limit corresponding to the treatment energy being provided to the instrument 10. As mentioned above, the current limit parameter corresponding to a treatment energy can be stored in the memory 26 and can be adjustable. Accordingly, when the controller (FIG. 2, 24) determines that the active and return electrodes of the instrument 10 are shorted together, the controller can access the current limit parameter corresponding to the energy setting and can reduce the current limit. In various embodiments, the current limit before the reduction can be approximately two amperes. In various embodiments, the reduced current limit can be approximately one ampere or approximately half an ampere or another value.

At step 410, the generator 20 receives further signals from the instrument over time relating to the load impedance of a load between the active and return electrodes. As with step 404, the signals can be return current returned from the instrument 10 to the generator 20 based on a non-therapeutic electrical waveform.

At step 412, the generator 20 uses the further signals to determine the load impedance and can determine that the load impedance is above a threshold indicative of the active and return electrodes no longer being shorted and no longer grasping tissue, such as approximately eight-thousand (8000) ohms. And at step 414, based on the determination that the load impedance is above the threshold, the generator 20 can reduce a voltage limit corresponding to the electrical energy being provided to the instrument.

Referring also to FIG. 2, the memory 26 can store various parameters for controlling the electrosurgical energy, such as power limit, voltage limit, current limit, ramp rate of power changes, ramp rate of voltage changes, and ramp rate of current changes, among other parameters. In various embodiments, these parameters are adjustable. In various embodiments, the power limit, the voltage limit, and the current limit are less than the maximum power, voltage, and current, respectively, that the generator 20 is capable of providing to the instrument.

In various embodiments, when the controller 24 reduces the current limit, the current being provided to the instrument may decrease based on the reduced current limit. The controller 24 can control the power supply 27 and the RF output stage 28 to reduce the current at a rate of approximately four and half amperes per second. When the controller 24 reduces the voltage limit, the voltage being provided to the instrument may decrease based on the reduced voltage limit. The controller 24 can control the power supply 27 and the RF output stage 28 to reduce the voltage at a rate of approximately nine-hundred volts per second.

Accordingly, what have been described are systems, methods, and devices for providing, controlling, and applying electrosurgical energy. Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator configured to provide electrical treatment energy to an instrument having an active electrode and a return electrode, the generator comprising:
   a processor; and
   a memory having stored thereon instructions which, when executed by the processor, cause the generator to:
      provide an indicated treatment energy to the instrument, the indicated treatment energy being set by a user and having a corresponding current limit;
      receive signals from the instrument over time relating to a load impedance between the active electrode and the return electrode of the instrument;
      determine based on a crest factor of the signals that the active electrode and the return electrode are currently shorted together and determine that, prior to the short, the instrument was grasping tissue between the active electrode and the return electrode, based on a a value of the crest factor; and
      based on the determination, reduce a current limit of treatment energy being provided to the instrument to below the corresponding current limit.

2. The electrosurgical generator of claim 1, wherein the corresponding current limit is less than a maximum current that is capable of being provided to the instrument.

3. The electrosurgical generator of claim 1, wherein in the determination, the memory stores further instructions which, when executed by the processor, causes the generator to determine that the instrument was grasping tissue based on the load impedance decreasing from above a threshold to below the threshold.

4. The electrosurgical generator of claim 3, wherein the load impedance threshold is approximately four ohms.

5. The electrosurgical generator of claim 1, further comprising an indicator configured to indicate that the active electrode and the return electrode are shorted, wherein the indicator is one of a visual indicator or an audio indicator.

6. The electrosurgical generator of claim 1, wherein the indicated treatment energy has a corresponding voltage limit, wherein the memory stores further instructions which, when executed by the processor, further cause the generator to:
   receive further signals from the instrument relating to the load impedance between the active electrode and the return electrode;
   determine based on the further signals that the load impedance is above a threshold; and
   based on the determination that the load impedance is above the threshold, reduce a voltage limit of treatment energy being provided to the instrument to below the corresponding voltage limit.

7. The electrosurgical generator of claim 6, wherein the corresponding voltage limit is less than a maximum voltage that is capable of being provided to the instrument.

8. The electrosurgical generator of claim 1, wherein in the determination, the memory stores further instructions which, when executed by the processor, causes the generator to determine that the instrument was grasping tissue based on the crest factor exceeding a predetermined threshold.

9. The electrosurgical generator of claim 1, wherein the signal includes a return current returned from the instrument to the generator based on a non-therapeutic waveform.

10. A method for providing electrical treatment energy to an instrument having an active electrode and a return electrode, the method comprising:
   providing an indicated treatment energy to the instrument, the indicated treatment energy being set by a user and having a corresponding current limit;
   receiving signals from the instrument over time relating to a load impedance between the active electrode and the return electrode of the instrument;
   determining based on a crest factor of the signals that the active electrode and the return electrode are currently shorted together and determine that, prior to the short, the instrument was grasping tissue between the active electrode and the return electrode, based on a value of the crest factor; and
   reducing, based on the determining, a current limit of treatment energy being provided to the instrument to below the corresponding current limit.

11. The method according to claim 10, wherein the corresponding current limit is less than a maximum current that is capable of being provided to the instrument.

12. The method according to claim 10, further comprising:
   determining that the instrument was grasping tissue based on the load impedance decreasing from above a threshold to below the threshold.

13. The method according to claim 12, wherein the load impedance threshold is approximately four ohms.

14. The method according to claim 10, wherein the indicated treatment energy has a corresponding voltage limit, further comprising:
   receiving further signals from the instrument relating to the load impedance between the active electrode and the return electrode;
   determining based on the further signals that the load impedance is above a threshold; and
   reducing, based on the determination that the load impedance is above the threshold, a voltage limit of treatment energy being provided to the instrument to below the corresponding voltage limit.

15. The method according to claim 14, wherein the corresponding voltage limit is less than a maximum voltage that is capable of being provided to the instrument.

16. A system for treating tissue, the system comprising:
   an electrosurgical instrument configured to receive electrical treatment energy and to treat tissue; and
   an electrosurgical generator including:
      a processor; and
      a memory having stored thereon instructions which, when executed by the processor, cause the generator to:
         provide an indicated treatment energy to the instrument, the indicated treatment energy being set by a user and having a corresponding current limit;
         receive signals from the instrument over time relating to a load impedance between the active electrode and the return electrode of the instrument;
         determine based on a crest factor of the signals that the active electrode and the return electrode are currently shorted together and determine that, prior to the short, the instrument was grasping tissue between the active electrode and the return electrode, based on a value of the crest factor; and
         based on the determination, reduce a current limit of treatment energy being provided to the instrument to below the corresponding current limit.

* * * * *